United States Patent [19]

Gross et al.

[11] Patent Number: 5,545,625
[45] Date of Patent: Aug. 13, 1996

[54] PREVENTING CONVERSION OF CITRULLINE TO ARGININOSUCCINATE TO LIMIT PATHOLOGICAL NITRIC OXIDE OVERPRODUCTION

[75] Inventors: Steven S. Gross, New York, N.Y.; Owen W. Griffith, Milwaukee, Wis.

[73] Assignee: The Medical College of Wisconsin Research Foundation, Inc., Milwaukee, Wis.

[21] Appl. No.: 354,585

[22] Filed: Dec. 12, 1994

[51] Int. Cl.$^6$ .................. A61K 31/70; A61K 31/195
[52] U.S. Cl. .................. 514/33; 514/561; 514/564; 514/930
[58] Field of Search .................. 514/33, 561, 564, 514/930

[56] References Cited

U.S. PATENT DOCUMENTS

| | | | |
|---|---|---|---|
| 4,775,623 | 10/1988 | Katsumata et al. | 435/114 |
| 5,028,627 | 7/1991 | Kilbourn et al. | 514/565 |
| 5,059,712 | 10/1991 | Griffith | 562/560 |
| 5,196,195 | 3/1993 | Griffith et al. | 424/94.6 |
| 5,216,025 | 6/1993 | Gross et al. | 514/565 |
| 5,364,881 | 11/1994 | Griffith et al. | 514/508 |
| 5,424,447 | 6/1995 | Griffith et al. | 594/74 |
| 5,464,858 | 11/1995 | Griffith et al. | 514/399 |

FOREIGN PATENT DOCUMENTS

WO95/01972  1/1995  WIPO .

OTHER PUBLICATIONS

Carignan, J. A., et al, Hosp. Formul. 21, 1025–1030 and 1033 (1986).
Corbett, J. A., et al, J. Clin. Invest. 90, 2384–2391 (1992).
Jinno, Y., et al, EMBL Database, Sequence from J. Biochem. 98, 1395–1403 (1985).
Kleeman, R., et al, FEBS, 328, 9–12 (Aug. 1993).
Nussler, A. K. et al, J. Biol. Chem., 269, 1257–1261 (1994).
Schmidt, H. H. H. W., et al, Eur. J. Pharmacol., 148, 293–295 (1988).
Corbett, J. A., et al, Proc. Natl. Acad. Sci. USA, 90, 1731–1735 (Mar. 1993).
Corbett, J. A., et al, Proc. Natl. Acad. Sci. USA, 90, 8992–8995 (Oct. 1993).
Kroncke, K–D, et al, Biochem. Biophys. Res. Commun. 175, 752–758 (1991).
Lukic, M. L., et al, Biochem. Biophys. Res. Commun. 178, 913–920 (1991).
Schmidt, H. H. H. W., et al, Eur. J. Pharmacol,. 154, 213–216 (1988).
Sessa, W. C., et al, Proc. Natl. Acad. Sci. USA, 87, 8607–8611 (Nov. 1990).
Corbett, J. A., et al, Biochemistry 32, 13767–13770 (1993).
Cross, A. H., et al, J. Clin. Invest. 93, 2684–2690 (1994).
McCartney–Francis, N., et al, J. Exp. Med. 178, 749–754 (1993).
Misko, T. P., et al, Eur. J. Pharmacol. 233, 119–125 (1993).
Suarez–Pinzon, W. L., et al, Endocrinology, 134, 1006–1010 (1994).
Takada, S., et al, J. Biochem. 85, 1309–1314 (1979).
Freytag, S. O., Medline Abstract of J. Biol. Chem., 259, 3160–6 (1984).
Grisolia, S., et al, The Urea Cycle, John Wiley & Sons, p. 191 (1976).
Mitchell, J. A., et al, Eur. J. Pharmacol., 182, 573–576 (1990).
Mulligan, M. S., et al, Proc. Natl. Acad. Sci. USA, 88, 6338–6342 (Jul. 1991).
Weinberg, J. B., et al, J. Exp. Med. 148, 651–660 (Feb. 1994).
Wu, G., et al, Biochem. J., 281, 45–48 (1992).
Hattori, Y., et al, J. Biol. Chem. 269, 9405–9408 (1994).
Ialenti, A., et al, Eur. J. Pharmacol. 211, 177–182 (1992).
Mulligan, M. S., et al, Br. J. Pharmacol., 107, 1159–1162 (1992).
Nathan, C. F., et al, Current Opinion in Immunology, 3, 65–70 (1991).
Yang, X., et al, J. Clin. Invest., 94, 714–721 (1994).

*Primary Examiner*—Kimberly Jordan

[57] ABSTRACT

Administration of argininosuccinate synthetase activity reducing agents, e.g., argininosuccinate synthetase induction blocking agents (e.g., antibiotics that bind to DNA sequences present in the upstream regulatory region of the argininosuccinate synthetase gene, such as mithramycin) and argininosuccinate synthetase inhibitors (e.g., L-citrulline antagonists such as methyl citrulline and L-aspartate antagonists such as D-aspartate) is useful to prevent or treat sepsis or cytokine-induced systemic hypotension, is useful in the treatment of sepsis or cytokine-induced systemic hypotension to restore vascular sensitivity to the effects of $\alpha_1$-adrenergic agonists, and is useful to suppress an immune response, e.g., in treating inflammation. In one embodiment, certain argininosuccinate synthetase activity reducing agents are used together with arginine antagonists to treat sepsis or cytokine induced hypotension.

35 Claims, 5 Drawing Sheets

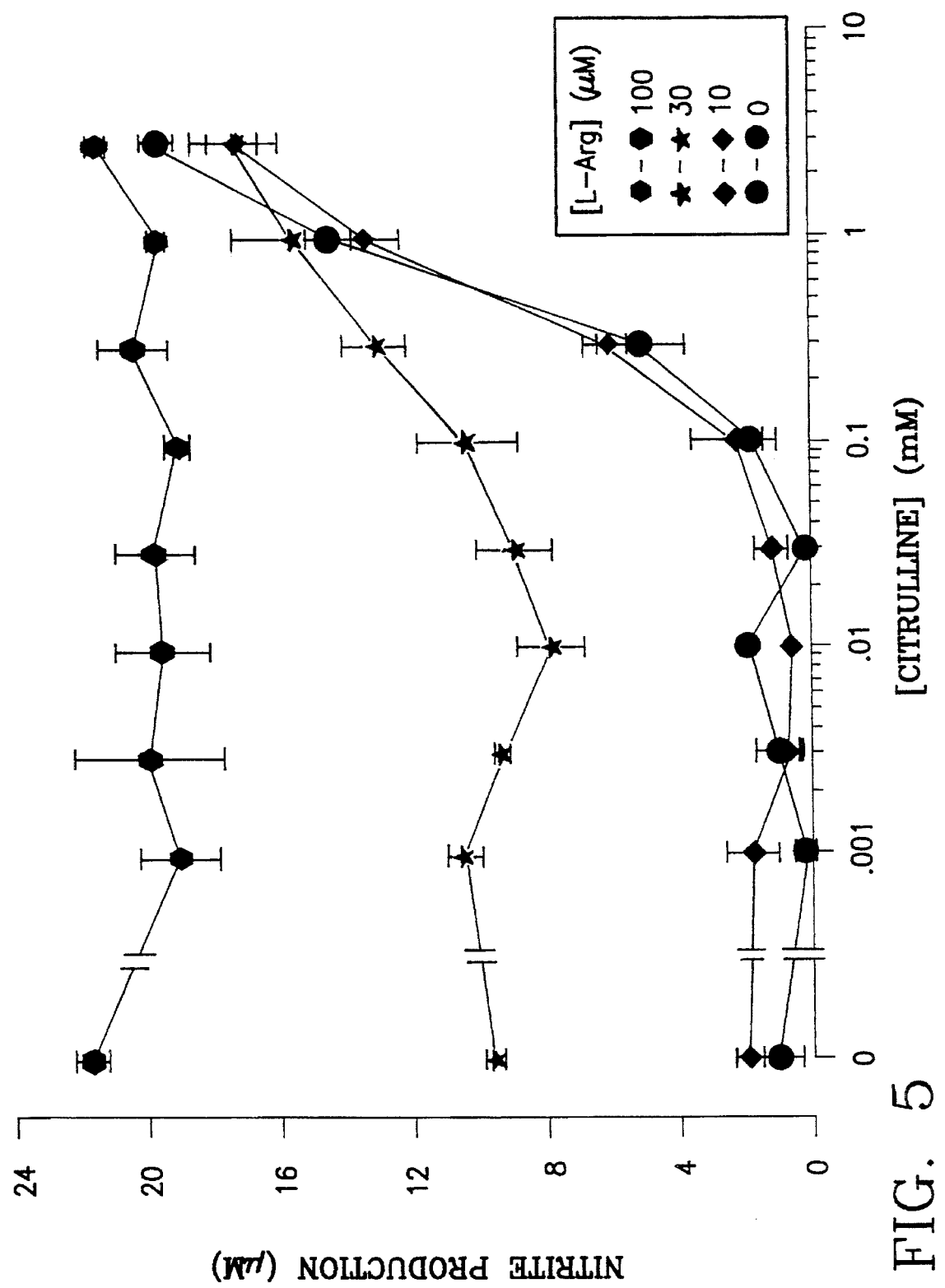

5,545,625

PREVENTING CONVERSION OF CITRULLINE TO ARGININOSUCCINATE TO LIMIT PATHOLOGICAL NITRIC OXIDE OVERPRODUCTION

This invention was made at least in part with Government support under National Institutes of Health Grant HL46403 and under National Institutes of Health Grant DK37116.

TECHNICAL FIELD

This invention is directed to a novel approach for inhibiting biological nitric oxide production.

BACKGROUND OF THE INVENTION

For several decades nitroglycerin has been administered to humans as a vasodilating agent in the treatment of cardiovascular disease. It has been shown that nitroglycerin so administered is converted in the body to nitric oxide which is the pharmacologically active metabolite. Recently, nitric oxide has been shown to be formed enzymatically as a normal metabolite from arginine in vascular endothelium to provide an important component of endothelium-derived relaxing factors (EDRFs) which are currently being intensively studied as participating in regulation of blood flow and vascular resistance. Macrophages have also been shown to produce nitric oxide in the body as a component of their cell killing and/or cytostatic function.

More recently it has been established that the enzyme forming nitric oxide from arginine, i.e., nitric oxide synthase, occurs in at least two distinct types, namely the constitutive forms and an inducible form. Constitutive forms are present in normal endothelial cells, neurons and some other tissues. Formation of nitric oxide by a constitutive form in endothelial cells is thought to play a role in normal blood pressure regulation. The inducible form of nitric oxide synthase has been found to be present in activated macrophages and is induced in endothelial cells and vascular smooth muscle cells, for example, by various cytokines and/or microbial products. It is thought that in sepsis or cytokine-induced shock, overproduction of nitric oxide by the inducible form of nitric oxide synthase plays an important role in the observed life-threatening hypotension. Furthermore, it is thought that overproduction of nitric oxide by the inducible form of nitric oxide synthase is a basis for insensitivity to clinically used pressor agents such as $\alpha_1$-adrenergic agonists in the treatment of septic or cytokine-induced shock patients. Moreover, it is thought that overproduction of nitric oxide by inducible form of nitric oxide synthase is involved in inflammation incident to an immune response.

Overproduction of nitric oxide is due either to overstimulation of a constitutive nitric oxide synthase (cNOS) or to overexpression of inducible nitric oxide synthase (iNOS). In either case, overproduction of nitric oxide is also dependent on adequate availability of arginine, the substrate of nitric oxide synthase. Arginine supply is maintained in three ways: (i) protein degradation, (ii) uptake of arginine from plasma, (iii) conversion of citrulline to arginine by pathways involving conversion of citrulline and aspartate to argininosuccinate (ASA) by argininosuccinate synthetase and conversion of ASA to arginine and fumarate by argininosuccinate lyase. In the case of iNOS, enzyme activity and overproduction of nitric oxide is also dependent on availability of required cofactors including tetrahydrobiopterin.

To date, pathological overproduction of nitric oxide has been controlled by administration of nitric oxide synthase inhibiting arginine antagonists, plasma arginine depleting enzymes and tetrahydrobiopterin induction or utilization blocking agents.

SUMMARY OF THE INVENTION

It has been discovered herein that administration of argininosuccinate synthetase activity reducing agents is useful to prevent or treat sepsis or cytokine-induced systemic hypotension, is useful in the treatment of sepsis or cytokine-induced systemic hypotension to restore vascular sensitivity to the effects of $\alpha_1$-adrenergic agonists, is useful to suppress an immune response, e.g., in treating inflammation, and is useful to prevent or treat a subject for a stroke.

One embodiment herein is directed to a method of prophylaxis or treatment of a subject for systemic hypotension caused by pathological overproduction of nitric oxide from arginine in vascular cells in said subject induced by therapy with a cytokine or by exposure to a bacterial endotoxin, said method comprising administering to a subject expected to develop or having such systemic hypotension a therapeutically effective amount of an argininosuccinate synthetase activity reducing agent. The agent can be either an argininosuccinate synthetase induction blocking agent or an argininosuccinate synthetase inhibitor. A therapeutically effective amount of an argininosuccinate synthetase activity reducing agent in this method is one that causes reduction in induced nitric oxide production to the extent of causing an increase in blood pressure.

Another embodiment herein is directed to a method for treatment of a subject for systemic hypotension caused by pathological overproduction of nitric oxide from arginine in vascular cells in said subject induced by therapy with a cytokine or by exposure to a bacterial endotoxin, said method comprising administering to a subject having such systemic hypotension a therapeutically effective amount of an $\alpha_1$-adrenergic agonist, and an amount of argininosuccinate synthetase activity reducing agent to restore vascular contractile sensitivity to the effects of said $\alpha_1$-adrenergic agonist. The argininosuccinate synthetase activity reducing agent can be either an argininosuccinate synthetase induction blocking agent or an argininosuccinate synthetase inhibitor. A therapeutically effective amount of $\alpha_1$-adrenergic agonist is one that causes increase in blood pressure.

Still another embodiment herein is directed to a method for treating a subject for systemic hypotension caused by pathological overproduction of nitric oxide from arginine in vascular cells in said subject induced by therapy with a cytokine or by exposure to a bacterial endotoxin, said method comprising administering to said subject a therapeutically effective amount of an arginine antagonist of nitric oxide synthesis by nitric oxide synthase and a therapeutically effective amount of an argininosuccinate synthetase activity reducing agent selected from the group consisting of argininosuccinate synthetase induction blocking agents and argininosuccinate synthetase inhibitors which do not block the activity of inducible nitric oxide synthase (by inhibiting inducible nitric oxide synthase by binding to it or its heme cofactor). The therapeutically effective amount of arginine antagonist of nitric oxide synthesis by inducible nitric oxide synthase is an induced nitric oxide production limiting amount, i.e., a blood pressure raising amount. The therapeutically effective amount of the argininosuccinate synthetase activity reducing agent in this method is that which when administered to a subject sufficiently limits the induction, or further induction, of argininosuccinate synthetase or inhibits the activity of argininosuccinate synthetase such that the induced argininosuccinate synthetase dependent citrulline to arginine metabolic pathway does not contribute significantly to the availability of arginine needed to sustain overproduction of nitric oxide by inducible nitric oxide synthase, thereby to potentiate duration or magnitude of the blood pressure increase caused by the administration of the arginine antagonist of nitric oxide synthesis by nitric oxide synthase.

Therapy with a cytokine includes therapy with interferons including interferon-gamma, tumor necrosis factor, interleukin-1 or interleukin-2, e.g., chemotherapeutic treatment with tumor necrosis factor or interleukin-2. Treatment with nitric oxide synthase inducing cytokines will cause systemic hypotension by pathological overproduction of nitric oxide if continued for a long enough period. Thus, the expectation of systemic hypotension caused by pathological overproduction of nitric oxide is currently a limitation on the extent and duration of cytokine therapy.

Bacterial endotoxin induced system hypotension, also known as sepsis or septic shock, may arise, e.g., from bacterial infection or immunosuppression therapy. There are subjects that are expected to develop this condition, i.e., who are at risk for developing this condition, e.g., those suffering from burn or hemorrhage or undergoing immunosuppression therapy.

In another embodiment, the invention herein is directed to a method of prophylaxis or treatment of a subject for inflammation caused by induced nitric oxide production from arginine in cells, said method comprising administering to a subject at risk for or having such inflammation, a therapeutically effective amount of an argininosuccinate synthetase activity reducing agent. The inflammation may arise, e.g., from non-acute allergic reactions including contact dermatitis, from autoimmune conditions including rheumatoid arthritis, myasthenia gravis, multiple schlerosis, lupus erythematosus and Parkinson's disease, and host-defense immune mechanisms, e.g., allograft rejection reactions, mediated by immunologically induced nitric oxide production. Those at risk for such condition, e.g., those of high probability to become afflicted with this condition include those undergoing allograft treatment. The agent can be either an argininosuccinate synthetase induction blocking agent or an argininosuccinate synthetase inhibitor. A therapeutically effective amount of an argininosuccinate synthetase activity reducing agent in this method is an amount which causes reduction in induced nitric oxide synthesis to the extent of suppressing the immune response that is part of the inflammatory response thereby attenuating the inflammation.

In another embodiment, the invention herein is directed to a method of prophylaxis or treatment of a subject for a stroke, said method comprising administering to said subject a therapeutically effective amount, e.g., a neuronal cell protecting amount, of an argininosuccinate synthetase activity reducing agent.

In another embodiment, the invention is directed at $N^\omega$-$C_{1-6}$-alkyl-L-citrullines as novel compounds.

The term "subject" is used herein to mean a mammal.

BRIEF DESCRIPTION OF THE DRAWINGS

FIG. 5 depicts graphs showing the effect on nitrite production in induced intact cells of varying the concentration of citrulline at fixed concentrations of arginine and depicts results of Example V.

DETAILED DESCRIPTION

Figure 1:
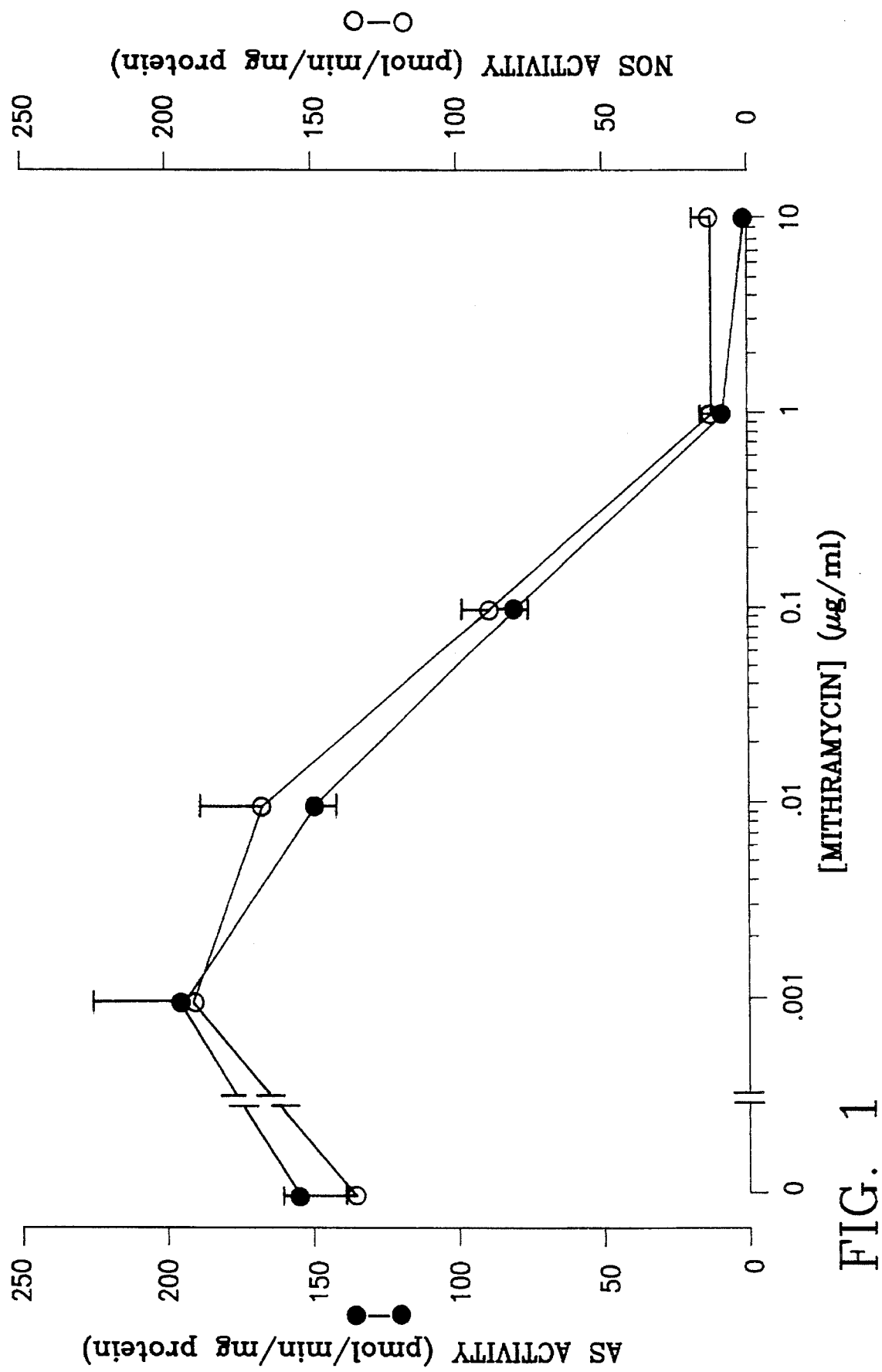
FIG. 1 is a graph of concentration of mithramycin versus argininosuccinate synthetase activity (filled in circles) and versus nitric oxide synthase activity (open circles) and depicts results of Example I.

The argininosuccinate synthetase activity reducing agents herein consist of argininosuccinate synthetase induction blocking agents and argininosuccinate synthetase inhibitors. They do not include agents which globally inhibit gene transcription such as actinomycin D, or agents which globally inhibit protein synthesis such as cycloheximide, or glucocorticoids.

The argininosuccinate synthetase induction blocking agents are preferably antibiotics that bind to DNA sequences present in the upstream regulatory region of the argininosuccinate synthetase gene (described in Freytag, S. O., et al, J. Biol. Chem., 259(5), 3160–3166, 3/84 and Jinno, Y., et al, J. Biochem. 98, 1395–1403, 1985 and is archived in The European Molecular Biology Database under EMBL accession number 03258), such as the sequences for the binding of the transcriptional activating factor SP1. Antibiotics known to do this include mithramycin (also known as plicamycin), chromomycins (e.g., chromomycin $A_3$) and olivomycins (e.g., olivomycins A, B, C and D). Some of these antibiotics also have been found to block the induction of nitric oxide synthase gene expression. Such antibiotics limit induced production of nitric oxide in two ways, namely by limiting induction of argininosuccinate synthetase resulting in limiting of production of substrate arginine from citrulline and also by limiting induction of nitric oxide synthase catalyst so that the conversion of arginine into nitric oxide and citrulline is limited. Administration of these antibiotics also has the effect of depleting calcium levels. However, this is not a problem when these antibiotics are administered to treat acute conditions (e.g., when used alone or together with $\alpha_1$-adrenergic agonists in treatment of sepsis or cytokine-induced hypotension) or for short term treatment for prophylaxis of expected induced hypotension or for short term treatment of inflammation.

The argininosuccinate synthetase inhibitors bind to argininosuccinate synthetase to block the activity thereof and thereby prevent the argininosuccinate synthetase from converting citrulline to argininosuccinate.

The argininosuccinate synthetase inhibitors can be, for example, L-citrulline antagonists, i.e., compounds which interfere with the action of argininosuccinate synthetase on L-citrulline, or L-aspartate antagonists, i.e., compounds which interfere with the action of argininosuccinate synthetase on L-aspartate.

The L-citrulline antagonists include, for example, L-thiocitrulline and L-homothiocitrulline which also block the activity of inducible nitric oxide synthase by binding to heme cofactor of inducible nitric oxide synthase (i.e., the catalytically important heme cofactor enfolded in a nitric oxide synthase molecule) and canavanine which also inhibits inducible nitric oxide synthase as well as L-citrulline antagonists different from L-thiocitrulline and L-homothiocitrulline and canavanine and which do not also block the activity of nitric oxide synthase by binding to inducible nitric oxide synthase or its heme cofactor, e.g., $N^\omega$-$C_{1-6}$-alkyl-L-citrullines, such as $N^\omega$-methyl-L-citrulline, and amino acids which naturally occur in mammalian species, except for arginine, preferably L-norvaline, L-isoleucine, L-valine and L-serine.

The L-aspartate antagonists include, for example, α-methyl-D-L-aspartate, D-aspartate, erythro-β-hydroxyl-DL-aspartate, threo-β-hydroxy-β-methyl-DL-aspartate and erythro-β-hydroxy-β-methyl-DL-aspartate.

For the embodiment where $\alpha_1$-adrenergic agonists are utilized, $\alpha_1$-adrenergic agonists are used for the same purpose now (i.e., to increase blood pressure in a hypotensive subject) but eventually stop working because of loss of vascular contractile sensitivity. The $\alpha_1$-adrenergic agonists include epinephrine, norepinephrine, dopamine, phenylephrine, metaraminol, methoxamine, ephedrine and nephentermine.

For the embodiment where arginine antagonists of nitric oxide synthesis by nitric oxide synthase are used, i.e., compounds which interfere with the action of iNOS on L-arginine, these bind to iNOS to block the activity thereof and thereby prevent the iNOS from converting arginine to nitric oxide and citrulline. The arginine antagonists contemplated are those which are not also argininosuccinate synthetase inhibitors. These include $N^G$-methyl-L-arginine, $N^G$-amino-L-arginine, $N^G$-nitro-L-arginine, $N^G$-nitro-L-arginine methyl ester, $N^\delta$-iminomethyl-L-ornithine, $N^6$-(hydrazinoiminomethyl)lysine, and guanidino substituted arginines or homoarginines based on monoalkyl carbon-substituted ornithines or lysines (as described in U.S. Pat. No. 5,281,627).

We turn now to the method herein for the prophylaxis or treatment of a subject for systemic hypotension caused by pathological overproduction of nitric oxide from arginine in vascular cells in said subject induced by therapy with a cytokine or by exposure to a bacterial endotoxin, said method comprising administering to a subject expected to develop or having such systemic hypotension a therapeutically effective amount of argininosuccinate synthetase activity reducing agent. We turn firstly to where argininosuccinate synthetase induction blocking agents are used as the argininosuccinate synthetase activity reducing agents. Mithramycin is utilized preferably at a dosage ranging from 15 to 25 µg/kg for acute treatments (e.g., treatment of hypotension resulting from septic shock) and 12 to 15 µg/kg for prophylaxis and may be administered intravenously as a bolus injection or as an infusion over 1 to 3 hours. Chromomycins are utilized preferably at a dosage ranging from about 15 to 26 µg/kg for acute treatments and 12 to 16 µg/kg for prophylactic treatments and may be administered intravenously. Olivomycins are utilized at a dosage preferably ranging from 15 to 200 µg/kg for acute treatments and 12 to 125 µg/kg for prophylaxis and may be administered intravenously. As these agents are known to lower plasma levels of calcium, calcium supplementation may be provided to patients in need thereof. For prophylaxis, the argininosuccinate synthetase induction blocking agents should be administered at the dosages recited for this purpose daily for no more than about 4 days. We turn now to where argininosuccinate synthetase inhibitors are used as the argininosuccinate synthetase activity reducing agents. Where L-citrulline antagonists are used as the argininosuccinate synthetase inhibitors, for treatment of systemic hypotension already occurring, these are administered in a blood pressure raising amount, generally 1 mg/kg to 100 mg/kg for L-enantiomer (preferably 2 mg/kg to 20 mg/kg for L-thiocitrulline and 2 mg/kg to 40 mg/kg for L-homothiocitrulline and 20 mg/kg to 100 mg/kg for $N^\omega$-methyl-L-citrulline) by a route of administration obtaining a fast response, normally parenteral, preferably intravenous, and for treatment in cases where systemic hypotension is expected (i.e., for prophylaxis, i.e., prevention or delay of the condition occurring or to provide reduced severity of the condition which occurs), these are administered to provide a plasma level of L-citrulline antagonist sufficient to eliminate or delay the occurring of the hypotension or reduce the severity of the hypotension which occurs, generally a plasma concentration of L-citrulline antagonist ranging from 1 µM to 1000 µM for L-enantiomer (preferably 10 µM to 50 µM for L-thiocitrulline and L-homothiocitrulline and 200 to 1000 µM for $N^\omega$-methyl-L-citrulline) by a route of administration which can be parenteral (e.g., intravenous) but also can be oral (doses to provide this concentration may be determined by considering the half-life of the compounds in the body). L-Citrulline antagonists can be administered for the same purposes by continuous infusion, in which case the doses would range from 1 mg/kg/hr to 100 mg/kg/hr generally, (preferably 2 mg/kg/hr to 20 mg/kg/hr for L-thiocitrulline and 2 mg/kg/hr to 40 mg/kg/hr for L-homothiocitrulline and 20 mg/kg/hr to 100 mg/kg/hr for $N^\omega$-methyl-L-citrulline). Where L-aspartate antagonists are used as the argininosuccinate synthetase inhibitors, for treatment of systemic hypotension already occurring, these are administered in a blood pressure raising amount, generally 10 mg/kg to 1000 mg/kg (preferably 10 mg/kg to 100 mg/kg for D-aspartate) by a route of administration obtaining a fast response, normally parenteral, preferably intravenous, and for treatment in cases where systemic hypotension is expected (i.e., for prophylaxis), these are administered to provide a plasma level of L-aspartate antagonist sufficient to eliminate or delay the occurring of the hypotension or reduce the severity of the hypotension which occurs, generally a plasma concentration of L-aspartate antagonist ranging from 50 µM to 1000 µM (preferably 50 µM to 200 µM for D-aspartate) by a route of administration which can be parenteral (e.g., intravenous) but also can be oral (doses to provide the concentration may be determined by considering the half-life of the compounds in the body). L-Aspartate antagonists can be administered for the same purposes by continuous infusion, in which case the doses would range from 10 mg/kg/hr to 1000 mg/kg/hr (preferably 10 mg/kg/hr to 100 mg/kg/hr for D-aspartate).

We turn now to the method herein for the treatment of a subject for systemic hypotension caused by pathological overproduction of nitric oxide from arginine in vascular cells in said subject induced by therapy with a cytokine or by exposure to a bacterial endotoxin, said method comprising administering to a subject having such systemic hypotension a therapeutically effective amount of an $\alpha_1$-adrenergic agonist and an amount of argininosuccinate synthetase activity reducing agent to restore vascular contractile sensitivity to the effects of the $\alpha_1$-adrenergic agonist, hereinafter referred to as the second method herein.

The $\alpha_1$-adrenergic agonists for the second method herein are used in the same dosages as they are now used for the same purpose (i.e., to increase blood pressure in a hypotensive patient), i.e., in conventional therapeutically effective amounts. Doses for the $\alpha_1$-adrenergic agonist dopamine typically range from 2 µg/kg/min to 50 µg/kg/min. Doses for the $\alpha_1$-adrenergic agonist norepinephrine typically range from 2 µg/min to 4 µg/min. Doses for the $\alpha_1$-adrenergic agonist phenylephrine can range from 0.1 to 10 µg/kg. The route of administration of the most popular $\alpha_1$-adrenergic agonists (norepinephrine and dopamine) is intravenous and for the others the route of administration is intravenous or in some cases subcutaneous.

We turn now to where argininosuccinate synthetase induction blocking agents are used as the argininosuccinate synthetase activity reducing agents in the second method herein. Mithramycin is utilized at a dosage preferably ranging from 15 to 25 µg/kg and may be administered intravenously as a bolus injection or as an infusion over 1 to 3 hours. Chromomycins are utilized preferably at a dosage ranging from about 15 to 26 µg/kg and may be administered intravenously. Olivomycins are utilized at a dosage preferably ranging from 15 to 200 µg/kg and may be administered intravenously.

We turn now to where argininosuccinate synthetase inhibitors are used as the argininosuccinate synthetase activity reducing agents in the second method herein. Where L-citrulline antagonists are used as the argininosuccinate synthetase inhibitors, these are administered in a vascular contractile sensitivity restoring amount, generally 1 mg/kg to 100 mg/kg for L-enantiomer (preferably 2 mg/kg to 20 mg/kg for L-thiocitrulline and L-homothiocitrulline and 20 mg/kg to 100 mg/kg for $N^\omega$-methyl-L-citrulline) by a route of administration obtaining a fast response, normally parenteral, preferably intravenous. L-Citrulline antagonists can be administered for the same purpose by continuous infusion, in which case the doses would range from 1 mg/kg/hr to 100 mg/kg/hr generally (preferably 2 mg/kg/hr to 20 mg/kg/hr for L-thiocitrulline and L-homothiocitrulline and 20 mg/kg/hr to 100 mg/kg/hr for $N^\omega$-methyl-L-citrulline). Where L-aspartate antagonists are used as the argininosuccinate synthetase inhibitors, these are administered in a vascular contractile sensitivity restoring amount, generally 10 mg/kg to 1000 mg/kg (preferably 10 mg/kg to 100 mg/kg for D-aspartate) by a route of administration obtaining a fast response, normally parenteral, preferably intravenous. L-Aspartate antagonists can be administered for the same purposes by continuous infusion in which case the doses would range from 10 mg/kg/hr to 1000 mg/kg/hr (preferably 10 mg/kg/hr to 100 mg/kg/hr for D-aspartate).

We turn now to the method herein for the treatment of a subject for systemic hypotension caused by pathological overproduction of nitric oxide from arginine in vascular cells in said subject induced by therapy with a cytokine or by exposure to a bacterial endotoxin, said method comprising administering to said subject a therapeutically effective amount of an arginine antagonist of nitric oxide synthesis by nitric oxide synthase and a therapeutically effective amount of an argininosuccinate synthetase activity reducing agent selected from the group consisting of argininosuccinate synthetase induction blocking agents and argininosuccinate synthetase inhibitors which do not block the activity of inducible nitric oxide synthase (by inhibiting inducible nitric oxide synthase by binding to it or its heme cofactor), hereinafter referred to as the third method herein.

The arginine antagonist competes with arginine for the active site of nitric oxide synthase. Therefore, lowering intracellular arginine level by administering an argininosuccinate synthetase activity reducing agent enables lowering the dosage of arginine antagonist necessary to limit induced nitric oxide production and raise blood pressure, e.g., to less than 50% of the dosage of arginine antagonist otherwise necessary. This diminishes the potential toxicity of the arginine antagonist.

The arginine antagonists are used in the third method herein in a blood pressure raising amount. The dosages generally range from 0.1 to 100 mg/kg and/or from 0.1 to 100 mg/kg/hr, with the actual dosage depending on the arginine antagonist selected. Doses for $N^G$-methyl-L-arginine range from 1 to 40 mg/kg and/or 1 to 40 mg/kg/hr. The route of administration is preferably intravenous or other route providing a fast response.

The argininosuccinate synthetase induction blocking agents for the third method herein are those generally described above. The argininosuccinate synthetase inhibitors which do not block the activity of inducible nitric oxide synthase (by inhibiting inducible nitric oxide synthase by binding to it or its heme cofactor) for the third method herein can be (1) L-citrulline antagonists which do not block the activity of iNOS by binding to iNOS or its heme cofactor, or (2) L-aspartate antagonists. The L-citrulline antagonists for the third method herein can be, for example, $N^{107}$-$C_{1-5}$-alkyl-L-citrullines such as $N^\omega$-methyl-L-citrulline and amino acids which naturally occur in mammalian-species, except for arginine, preferably L-norvaline, L-isoleucine, L-valine and L-serine. L-Aspartate antagonists are generally described above.

Argininosuccinate synthetase activity reducing agents are used in the third method herein in an amount such that the induced argininosuccinate synthetase dependent citrulline to arginine metabolic pathway does not contribute significantly to the availability of arginine needed to sustain overproduction of nitric oxide by nitric oxide synthase, as may be determined by the ability to administer less arginine antagonist to achieve the same result as administering more arginine antagonist without the argininosuccinate synthetase activity reducing agent being administered.

We turn now to when argininosuccinate synthetase induction blocking agents are used as the argininosuccinate synthetase activity reducing agents in the third method herein. Mithramycin is utilized preferably at a dosage ranging from about 12 to 15 µg/kg and may be administered intravenously as a bolus injection or as an infusion over 1 to 3 hours. Chromomycins are utilized preferably at a dosage ranging from about 15 to 26 µg/kg and may be administered intravenously. Olivomycins are utilized preferably at a dosage ranging from about 12 to 125 µg/kg and may be administered intravenously.

We turn now to where argininosuccinate synthetase inhibitors which do not block the activity of inducible nitric oxide synthase are used in the third method herein. The L-citrulline antagonists are generally administered in a dosage of 1 mg/kg to 100 mg/kg (preferably 20 mg/kg to 100 mg/kg for $N^\omega$-methyl-L-citrulline) by a route of administration obtaining a fast response, normally parenteral, preferably intravenous. The L-citrulline antagonists can be administered for the same purpose by continuous infusion, in which case the doses would range from 1 mg/kg/hr to 100 mg/kg/hr generally (preferably, 20 mg/kg/hr to 100 mg/kg/ hr for N^ω-methyl-L-citrulline. The L-aspartate antagonists are generally administered in a dosage of 10 mg/kg to 1000 mg/kg (preferably 10 mg/kg to 100 mg/kg for D-aspartate) by a route of administration obtaining a fast response, normally parenteral, preferably intravenous. The L-aspartate antagonists can be administered for the same purposes by continuous infusion, in which case the doses would range from 10 mg/kg/hr to 1000 mg/kg/hr (preferably 10 mg/kg/hr to 100 mg/kg/hr for D-aspartate.

We turn now to the method herein of prophylaxis or treatment of a subject for inflammation caused by induced nitric oxide production from arginine in immune cells, said method comprising administering to a subject at risk for or having such inflammation, a therapeutically effective amount of an argininosuccinate synthetase activity reducing agent, hereinafter referred to as the fourth method herein.

We turn now to where argininosuccinate synthetase induction blocking agents are utilized as the argininosuccinate synthetase activity reducing agents in the fourth method herein. Mithramycin is utilized at a dosage ranging from about 0.1 to 50 μg/kg, for intravenous administration preferably at a dosage ranging from about 12 to 15 μg/kg. Chromomycins are utilized at a dosage ranging from about 0.1 to 50 μg/kg, for intravenous administration preferably at a dosage ranging from about 12 to 16 μg/kg. Olivomycins are utilized at a dosage ranging from about 0.1 to 125 μg/kg, for intravenous administration preferably ranging from about 12 to 125 μg/kg. Methods of administration include oral, intramuscular, subcutaneous, intrasynovial and intravenous. The dosages set forth are daily dosages and are administered for prophylaxis purposes or for a period of time to cause suppression of immune response and attenuation of inflammation, normally 2 days or more but for no more than 7 days.

We turn now to where argininosuccinate synthetase inhibitors are utilized as the argininosuccinate synthetase activity reducing agents in the fourth method herein. Where L-citrulline antagonists are used as the argininosuccinate synthetase inhibitors, for treatment of inflammation, these are administered in an inflammation attenuating amount, generally 0.01 mg/kg to 100 mg/kg and/or 0.01 mg/kg/hr to 100 mg/kg/hr for L-enantiomer (preferably 0.1 mg/kg to 20 mg/kg and/or 0.1 mg/kg/hr to 20 mg/kg/hr for L-thiocitrulline and L-homothiocitrulline and 0.2 mg/kg to 100 mg/kg and/or 0.2 mg/kg/hr to 100 mg/kg/hr for N^ω-methyl-L-citrulline). Where L-citrulline antagonists are used as the argininosuccinate synthetase inhibitors, for prophylaxis of inflammation from induced production of nitric oxide, these are administered to provide a plasma level of L-citrulline antagonist sufficient to eliminate or delay the occurring of inflammation from induced nitric oxide production or reduce the severity of the inflammation which occurs, generally a plasma concentration of L-citrulline antagonist ranging from 1 μM to 1000 μM for L-enantiomer (preferably 10 μM to 50 μM for L-thiocitrulline and L-homothiocitrulline and 200 to 1000 μM for N^ω-methyl-L-citrulline). Where L-aspartate antagonists are used as the argininosuccinate synthetase inhibitors, these are administered in an inflammation attenuating amount, generally 0.1 mg/kg to 1000 mg/kg and/or 0.1 mg/kg/hr to 1000 mg/kg/hr (preferably 0.1 mg/kg to 100 mg/kg and/or 0.1 mg/kg/hr to 100 mg/kg/hr for D-aspartate). Where L-aspartate antagonists are used as the argininosuccinate synthetase inhibitors, for prophylaxis of inflammation from induced production of nitric oxide, these are administered to provide a plasma level of L-aspartate antagonist sufficient to eliminate or delay the occurring of inflammation from induced nitric oxide production or reduce the severity of the inflammation which occurs, generally a plasma concentration of L-aspartate antagonist ranging from 50 to 1000 μM (preferably 50 to 200 μM for D-aspartate). Methods of administration include oral, intramuscular, subcutaneous, intrasynovial and intravenous. The dosages recited, which may be repeated, are administered for a period of time to cause suppression of immune response and attenuation of inflammation, i.e., treating for two days or more, e.g., for two to three weeks. For prophylaxis, doses to provide the aforestated plasma concentrations may be determined by considering the half-life of the compounds in the body.

The invention is illustrated in the following examples.

EXAMPLE I

Aortic smooth muscle cells were cultured by explanting segments of the medial layer of aortae from adult male Fischer 344 rats. Aortae were removed aseptically and freed of adventitial and endothelial cells by scraping both the lumenal and abluminal surfaces. Medial fragments (1–2 mm) were allowed to attach to dry Primaria 25 cm² tissue culture flasks (Falcon; Oxnard, Calif.) which were kept moist with growth medium until cells emerged. Cultures were fed twice weekly with medium 199 containing 10% fetal bovine serum, 25 mM HEPES, 2 mM L-glutamine, 40 μg/ml endothelial cell growth supplement (Biomedical Technologies; Stoughton, Mass.) and 10 μg/ml gentamycin (GIBCO; Grand Island, N.Y.). When primary cultures became confluent, they were passaged by trypsinization and the explants were discarded. Cells in passage 10–15 were seeded at 20,000/well in 96-well plates.

When the cells became confluent (density of $60-80 \times 10^3$ cells in a well), the medium was removed by suction and fresh medium consisting of 200 μl of RPMI 1640 (Whittaker Laboratories) containing 10% bovine calf serum, 2.5 mM glutamine and penicillin (80 U/ml), streptomycin (80 μg/ml) and fugizone (2 μg/ml) was added to each well via a pipette.

Groups of 4 wells were administered fixed concentrations of mithramycin (0.001 to 10 μg/ml); control wells received no mithramycin. To each was also added bacterial lipopolysaccharide (endotoxin); Serotype: *E. Coli.* 0111:B4, 30 μg/ml) plus rat interferon-gamma (50 ng/ml). The wells were then incubated at 37° C. in a humidified incubator for 24 hours. Cells were then harvested and prepared for assay of argininosuccinate synthetase (AS activity) and nitric oxide synthase (NOS activity).

Nitric oxide formation by smooth muscle cell cytosol was measured using a spectrophotometric kinetic microplate assay based on the increase in $A_{405}$ accompanying the oxidation of $Fe^{2+}$-myoglobin by nitric oxide. Cytosol (50–100 μg of protein) was incubated with 40 μm dithionite-reduced myoglobin (prepared as described in Gross, S. S., et al, Biochem. Biophys. Res. Commun. 160,881–886, 1989) in assay buffer containing 80 mM Tris, 0.5 mM L-arginine, 0.5 mM NADPH, and 10 μm tetrahydrobiopterin (pH 7.6). Assays were performed in triplicate with $A_{405}$ recorded for each sample every 18 seconds for a period of 15 minutes. The rate of nitric oxide synthesis was calculated from the rate of increase in $A_{405}$ by linear regression analysis. The conversion factor relating $A_{405}$ to the nitric oxide synthesis rate under the conditions employed was 1.05 milli optical density units (also referred to as mOD) $min^{-1}$ $pmol^{-1}$ of nitric oxide formed.

Argininosuccinate synthetase activity was assayed based on the conversion of [$^{14}$C]aspartate to [$^{14}$C]argininosuccinate, as described in O'Brien, W. E., Biochemistry 18, 5353–5356, 1979, with the exception that aspartate was present at a concentration of 30 μm (0.021 μCi/nmol). Reaction mixtures also contained L-citrulline (5 mM), Tris (10 mM, pH 7.5), ATP 0.1mM), phosphoenolpyruvate (1.5 mM), pyruvate kinase (4.5 units), myokinase (4 units), and pyrophosphatase (0.2 unit) in a total volume of 0.3 ml. Reactions were allowed to proceed for 90 minutes at 37° C before termination and quantification of the [$^{14}$C]argininosuccinate formed, using ion exchange chromatography on Dowex 1-X8 (200–400 mesh, Bio-Rad).

The results are shown in FIG. 1 where the filled in circles denote argininosuccinate synthetase (denoted AS in FIG. 1) activity and the open circles denote nitric oxide synthase (denoted NOS in FIG. 1) activity.

FIG. 1 shows that mithramycin, as a function of its concentration blocks argininosuccinate synthetase activity as well as nitric oxide synthase activity. The concentrations of mithramycin that are effective in this regard are the same concentrations obtained in patients administered doses of mithramycin for hypercalcemia as described in The Merck Manual, 16th edition, page 1013.

Similar results of blocking argininosuccinate synthetase activity as a function of concentration are obtained using the same concentrations of chromomycins and with up to 5 times greater concentrations of olivomycins.

EXAMPLE II

Figure 2:
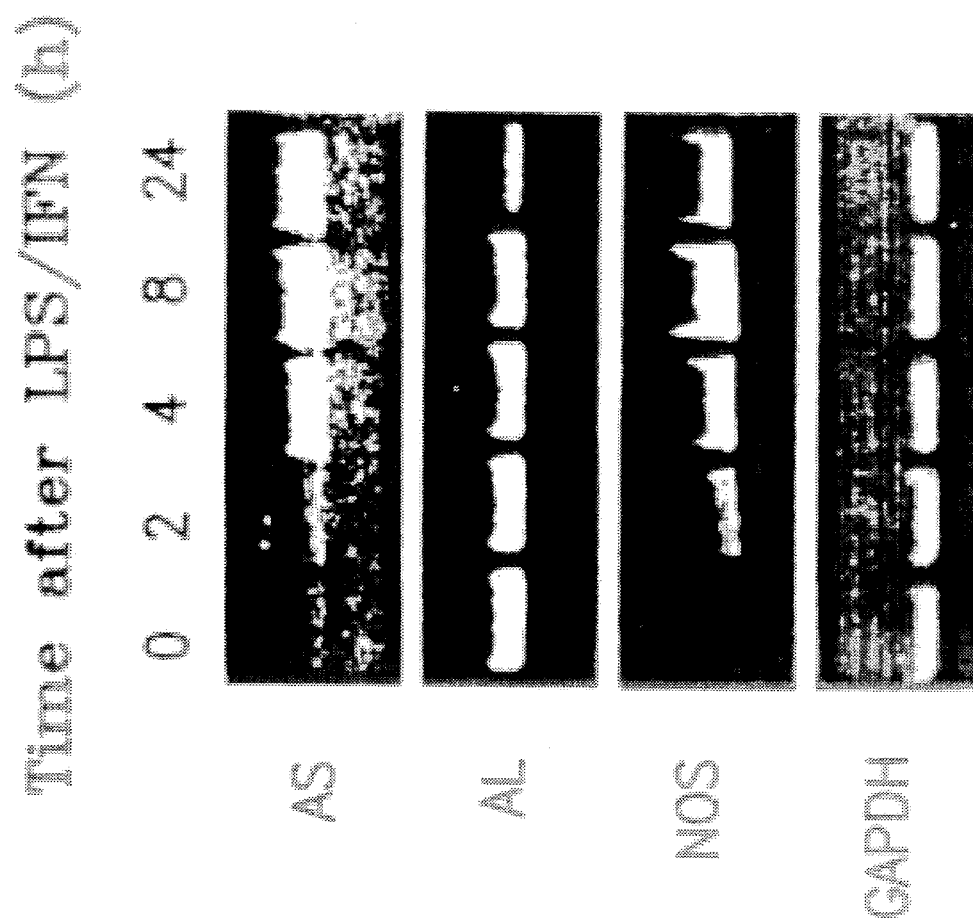
FIG. 2 shows the time course of lipopolysaccharide/interferon-gamma-induced changes in mRNA levels for argininosuccinate synthetase (AS), argininosuccinate lyase (AL), nitric oxide synthase (NOS) and glyceraldehyde-3-phosphate dehydrogenase (GAPDH) and depicts results of Example II.

Rat aortic smooth muscle cells were grown as described in Example I and were treated with 30 μg/ml bacterial lipopolysaccharide in combination with 50 ng/ml interferon-gamma. At the indicated times as shown in FIG. 2, cells were harvested and RNA was prepared and assayed by reverse transcriptase-polymerase chain reaction using gene specific primers. RNA was extracted by a modified guanidinium isothiocyanate method (RNAzol; Cinna/Biotecz, Houston, Tex.). Reverse transcriptase-polymerase chain reaction was performed by standard methods using 1 μg of total RNA. This was followed by polymerase chain reaction amplification using synthetic gene-specific primers for rat argininosuccinate synthetase as described in Amaya, Y., et al, J. Biochem. (Tokyo) 103, 177–181 (1988), for argininosuccinate lyase as described in Surh, L. C., et al, Nucleic Acids Research, 16, 9352 (1988) and murine-inducible nitric oxide synthase as described in Lyons, C. R., et al, J. Biol. Chem. 267, 6370–6374 (1992). The primers are specifically described in Hattori, Y., et al, J. Biol. Chem. 269, 9405–9408 (1994). Polymerase chain reaction amplification was performed according to the following schedule: denaturation, annealing, and elongation at 95, 55 and 72° C. for 30 sec, 30 sec and 1 min, respectively, for 30 cycles. Parallel amplification of glyceraldehyde-3-phosphate dehydrogenase was performed for reference using primers as described in Terada, Y., et al, J. Clin. Invest. 90, 659–665 (1992). Polymerase chain reaction products were electrophoresed on a 1.5% agarose gel containing ethidium bromide and visualized by UV-induced fluorescence. All polymerase chain reactions resulted in the amplification of a single product of the predicted size for argininosuccinate synthetase (612 bp), argininosuccinate lyase (600 bp) and nitric oxide synthase (807 bp). To confirm the identity of the polymerase chain reaction products, the products were cut with EcoRI and found to each give two fragments of the expected sizes based on reported sequences for rat argininosuccinate synthetase as described in Amaya, Y., et al, J. Biochem. (Tokyo) 103, 177–181 (1988) and for rat argininosuccinate lyase as described in Surh, L. C., et al, Nucleic Acids Res. 16, 9352 (1988). Subcloning and dideoxynucleotide sequencing of the polymerase chain reaction product for nitric oxide synthase revealed a sequence that was identical to the cloned cDNA from cytokine-activated rat aortic smooth muscle as described in Nunokawa, Y., et al, Biochem. Biophys. Res. Commun. 191, 89–94 (1993).

The results are shown in FIG. 2 wherein "LPS/IFN" stands for bacterial lipopolysaccharide/interferon-gamma; "AS" stands for argininosuccinate synthetase; "AL" stands for argininosuccinate lyase; "NOS" stands for nitric oxide synthase; and "GAPDH" stands for glyceraldehyde-3-phosphate dehydrogenase.

FIG. 2 shows that argininosuccinate synthetase mRNA is not normally present at detectable levels in rat aortic smooth muscle cells but appears on treatment with immunostimulants when nitric oxide synthase mRNA appears. It further shows that argininosuccinate lyase mRNA is initially present at detectable levels. Thus, the induced argininosuccinate synthetase endows the cells with the capacity to recycle citrulline into arginine.

EXAMPLE III

Figure 3:
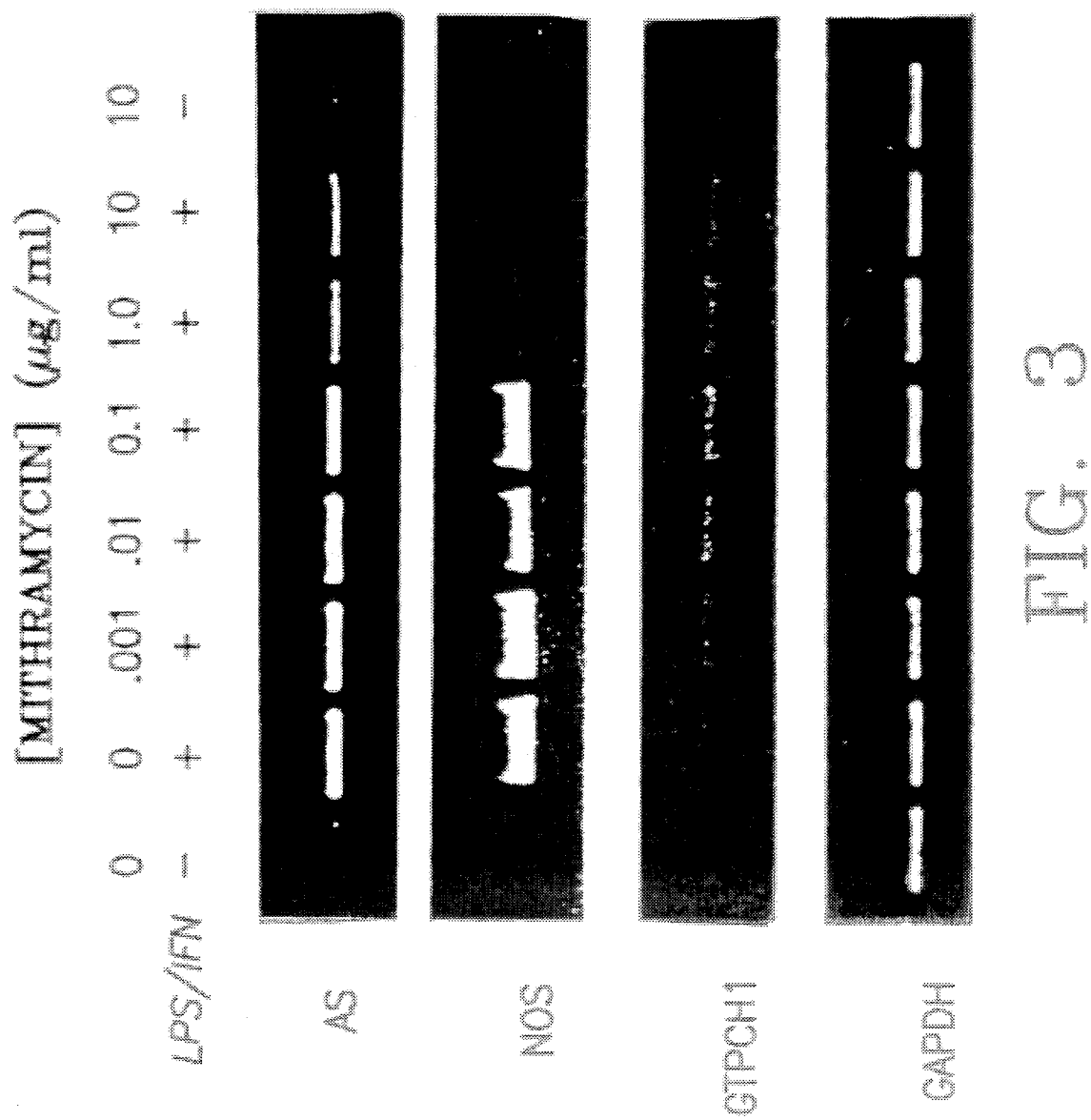
FIG. 3 effect of the change concentration of mithramycin on levels of argininosuccinate synthetase mRNA and nitric oxide synthase mRNA and on GTP cyclohydrolase I mRNA in induced rat aortic smooth muscle cells as determined by reverse transcriptase-polymerase chain reaction analysis and depicts results of Example III.

Rat aortic smooth muscle cells were grown as described in Example I and were untreated or treated with 30 μg/ml bacterial lipopolysaccharide in combination with 50 ng/ml interferon-gamma alone and with the concentrations of mithramycin indicated in FIG. 3. After 6 hours, cells were harvested and RNA was prepared and assayed by reverse transcriptase-polymerase chain reaction as described in Example II. Results using primers specific for glyceraldehyde-3-phosphate dehydrogenase as described in Example II and other primers specific for GTP cyclohydrolase I as described in Hattori, Y., et al, Biochem. Biophys. Res. Comm. 195, 435–441 (1993) are shown for comparison.

The results are depicted in FIG. 3 wherein "LPS/IFN" stands for bacterial lipopolysaccharide/interferon gamma; "AS" stands for argininosuccinate synthetase; "AL" stands for argininosuccinate lyase, "NOS" stands for nitric oxide synthase; "GTPCHi" stands for GTP cyclohydrolase I; and "GAPDH" stands for glyceraldehyde-3-phosphate dehydrogenase.

FIG. 3 shows that mithramycin inhibits gene transcription of argininosuccinate synthetase and nitric oxide synthase but not of GTP cyclohydralase I, i.e., that mithramycin does not block all gene transcription but selectively inhibits transcription of argininosuccinate synthetase and nitric oxide synthase.

EXAMPLE IV

Rat aortic smooth muscle cells were grown as described in Example I and were continuously treated with 30 μg/ml of bacterial lipopolysaccharide in combination with 50 ng/ml of interferongamma. Concentrations of mithramycin as indicated in FIG. 4 were added either simultaneously with immunostimulant (filled in circles in FIG. 4) or 4 hours later (open circles in FIG. 4).

Nitrite was used as an indicator of cellular NO synthesis and assay was carried out as described in Gross, S. S., et al, J. Biol. Chem. 267, 25722–25729 (1992). In the assay, cells were treated with serum- and arginine-free RPMI 1640 medium containing the desired test agents for 24 hours. The accumulation of nitrite in the cell culture medium was quantified colorimetrically after adding 100 μl of Griess reagent (1% sulfanilamide and 0.1% naphthalene diamine in 5% o-phosphoric acid) to an equal volume of sample.

Figure 4:
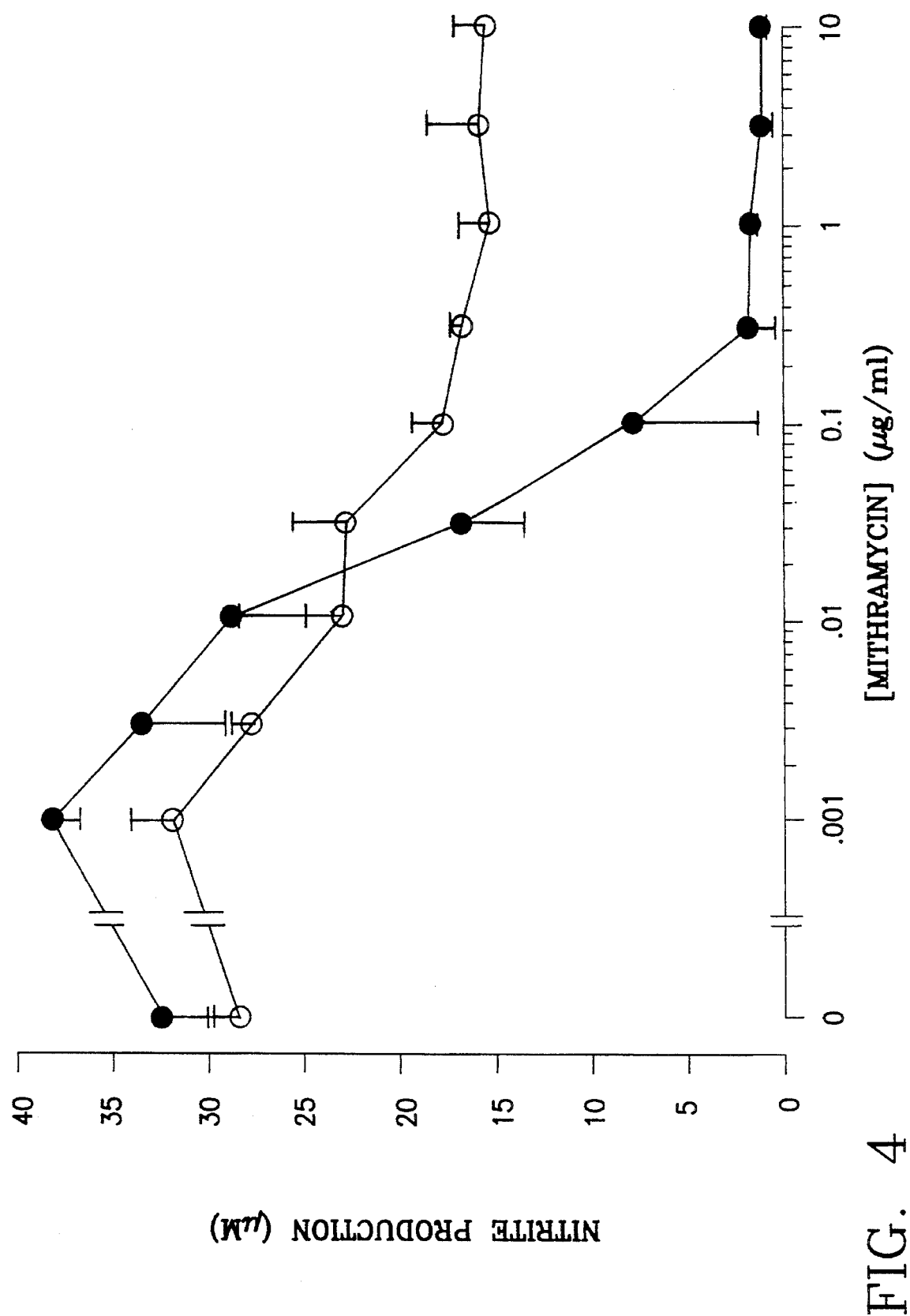
FIG. 4 depicts graphs of mithramycin concentration versus nitrite production with mithramycin administered post LPS/interferon gamma administration (open circles) and administered concurrently with LPS/interferon gamma (closed circles), and depicts results of Example IV.

The results are shown in FIG. 4 where points are mean values ± standard error of mean (n= 4) for nitrite accumulation in the cell culture medium after 24 hours. The results show that mithramycin inhibits induction of NO synthetic activity but is not a direct inhibitor of argininosuccinate synthetase or nitric oxide synthase. This is indicated because the results show that if induction is allowed to proceed for 4 hours so that argininosuccinate synthetase and nitric oxide synthase are present, mithramycin effectiveness to block NO production is markedly diminished.

Similar results indicating blocking of induction but failure to inhibit enzyme activities is shown when chromomycins in the same concentrations or olivomycins in concentrations up to five times higher replace mithramycin.

EXAMPLE V

Rat aortic smooth muscle cells were grown as described in Example I and were treated with 30 μg/ml of bacterial lipopolysaccharide in combination with 50 ng/ml of interferon-gamma. Concentrations of L-citrulline and L-arginine as indicated in FIG. 5 were added simultaneously with immunostimulant. Nitrite was used as an indicator of cellular NO synthesis and assay therefor was carried out as described in Example IV.

The results are shown in FIG. 5 where points are mean values ± standard error of mean (n=4) of nitrite concentration measured in the cell culture medium after 24 hours.

The results show that, due to induction of argininosuccinate synthetase activity, cells can utilize L-citrulline just as efficiently as L-arginine to provide a substrate for nitric oxide production. When there is 0 or low L-arginine, maximal nitrite is obtained (i.e., the same nitrite production as with unlimited arginine) if the concentration of L-citrulline is sufficiently high. Thus blocking L-citrulline synthesis diminishes cells' capacity to make nitric oxide since L-arginine is being consumed by nitric oxide synthase.

Cells normally obtain L-arginine from diet or via circulation from synthesis in the kidney. While some L-arginine is supplied by the kidney, it is not the maximally usable amount. The experiment shows that cells can make L-arginine from L-citrulline to supply the maximally usable amount.

EXAMPLE VI

Immunostimulant treated rat aortic smooth muscle cells prepared as in Example I were homogenized in 10 volumes (10 ml/gm rat aortic smooth muscle cells) of 100 mM tris buffer containing 1 mM phenylmethylsulfonyl fluoride (a protein synthesis inhibitor) and 1 mM dithiothreitol (to maintain enzyme in reduced form).

For the control, the crude homogenate was assayed for argininosuccinate synthetase by the procedure as described in Example I except that L-citrulline was present at a concentration of 150 μM instead of 5 mM. In duplicate runs, counts per minute were 534.00 (8.65% error) and 443.00 (9.50% error) counts per minute.

When L-thiocitrulline was included at a concentration of 1 mM, counts per minute in the argininosuccinate synthetase assay in duplicate runs were 272.00 (12.13% error) and 227.00 (13.27% error) counts per minute.

When L-canavanine was included at a concentration of 1 mM, counts per minute in the argininosuccinate synthetase assay in duplicate runs were 355.00 (10.61% error) and 393.00 (10.09% error) counts per minute.

When $N^{\omega}$-methyl-L-arginine was included at a concentration of 1 mM, counts per minute in the argininosuccinate synthetase assay in duplicate runs were 591.00 (8.23% error) and 520.00 (8.77% error) counts per minute.

The background count to be subtracted from the above count results was obtained by omitting citrulline from the argininosuccinate synthetase assay and in three runs was determined to be 217, 237 and 252 counts per minute.

The experiment shows that L-thiocitrulline and L-canavanine are inhibitors of immunostimulant induced argininosuccinate synthetase in rat aortic smooth muscle cells but that $N^G$-methyl-L- arginine is not.

When $N^{\omega}$-methyl-L-citrulline at a concentration of 1 mM is included, inhibition of immunostimulant induced argininosuccinate synthetase is shown which is more potent than obtained with L-canavanine but less potent than obtained with L-thiocitrulline is obtained.

When L-norvaline at a concentration of 1 mM is included, inhibition of immunostimulant induced argininosuccinate synthetase is shown.

When D-aspartate at a concentration of 1 mM is included, inhibition of immunostimulant induced argininosuccinate synthetase is shown.

EXAMPLE VII

A patient with Gram negative septicemia and blood pressure of 80/55 mm Hg is administered mithramycin at a dose of 25 μg/kg intravenously in 50 ml of saline over a 3 to 6 hour interval. The blood pressure returns to normal range within 12 to 48 hours.

Similar results are obtained when chromamycin antibiotic complex at a dose of 25 μg/kg or olivomycin antibiotic complex at a dose of 50 μg/kg is substituted for the mithramycin.

EXAMPLE VIII

A human is treated for renal cell cancer with interleukin-2 ($1 \times 10^6$ units) for 5 days. By the fifth day, the patient's blood pressure falls to 80/55 mm Hg and the patient encounters nausea and extreme discomfort. Three weeks later, the patient returns for a second course of interleukin-2 treatment but is pretreated (before commencing interleukin-2 infusion) with mithramycin (25 μg/kg) and is treated at 24 hour intervals thereafter with 25 μg/kg of mithramycin. The mithramycin is administered intravenously in 50 ml saline over a 3 to 6 hour interval. When mithramycin is administered, hypotension does not develop.

Similar results to what are obtained with mithramycin are obtained when chromomycin antibiotic complex at a dose of 25 μg/kg or olivomycin antibiotic complex at a dose of 50 μg/kg is substituted for the mithramycin.

EXAMPLE IX

A patient with Gram negative septicemia and blood pressure of 80/55 mm Hg is administered dopamine at 10 μg/kg/min to acutely increase blood pressure and concurrently is administered mithramycin (25 μg/kg) intravenously in 50 ml saline over 3–6 hours. Blood pressure increases

EXAMPLE X

A patient with Gram negative septicemia and blood pressure of 80/55 mm Hg is administered $N^G$-methyl-L-arginine in a bolus dose of 20 mg/kg intravenously in saline and thereafter is given a sustained infusion of $N^G$-methyl-L-arginine at a dosage of 10 mg/kg/hr. Mithramycin (25 µg/kg) is given intravenously in 50 ml saline over 3–6 hours starting at the time of the bolus dose of $N^G$-methyl-L-arginine. Blood pressure becomes normotensive within minutes of administration of the bolus dose of $N^G$-methyl-L-arginine and the normotensive state is sustained. The patient is released after 2 days.

Similar results to what are obtained with mithramycin are obtained when chromomycin antibiotic complex at a dose of 25 µg/kg or olivomycin antibiotic complex at a dose of 50 µg/kg is substituted for the mithramycin.

EXAMPLE XI

A patient with rheumatoid arthritis with swelling localized to two painful joints is administered mithramycin at a dosage of 0.25 µg/kg intra-articularly into each joint. Local synovitis is reduced in 12 to 24 hours.

Similar results to what are obtained with mithramycin are obtained when chromomycin antibiotic complex at a dose of 0.25 µg/kg or olivomycin antibiotic complex at a dose of 0.50 µg/kg is substituted for the mithramycin.

EXAMPLE XII

Sprague-Dawley rats are injected with 25 cc air subdermally in the dorsal area in accordance with the air pouch inflammatory model (Selye, H., Proc. Soc. Exper. Biol. and Med., 82, 328–333 (1953). Into the air pouch formed, an inflammatory stimulus, croton oil (0.5% in 0.5 ml corn oil), is injected. The rats in one group do not receive drug. The rats in the second group receive mithramycin at 25 µg/kg intraperitoneally with repeat doses at 24 hour intervals. At the end of 5 days, the group of rats given mithramycin have significantly less nitrite in the fluid exudate contained in the granulomycous lesion and less inflammation than the rats in the other group.

Similar results to what are obtained with mithramycin are obtained when chromomycin antibiotic complex at a dose of 25 µg/kg or olivomycin antibiotic complex at a dose of 50 µg/kg is substituted for the mithramycin.

EXAMPLE XIII

A patient with Gram negative septicemia and blood pressure of 80/55 mm Hg is administered L-thiocitrulline in a bolus dose of 20 mg/kg intravenously in saline and thereafter is given a sustained infusion of L-thiocitrulline at a dose of 10 mg/kg/hr. Blood pressure becomes normotensive within 5 to 10 minutes of administration of the bolus dose of L-thiocitrulline and the normotensive state is sustained. The patient is released after 2 days.

Similar results are obtained to what are obtained with L-thiocitrulline, when L-homothiocitrulline is used at double the dose for L-thiocitrulline. When $N^G$-methyl-L-citrulline or L-norvaline or L-isoleucine is used at quadruple the dose for L-thiocitrulline or D-aspartate is used at double the dose for L-thiocitrulline, blood pressure is raised within about 1 to 4 hours of administration of the bolus dose.

EXAMPLE XIV

A human is treated for renal cell cancer with interleukin-2 ($1 \times 10^6$) for 5 days. Simultaneously with commencing interleukin-2 infusion, L-thiocitrulline (10 mg/kg/day) is administered. Hypotension does not develop.

Similar results to what are obtained with L-thiocitrulline are obtained with the double dose for L-thiocitrulline of D-aspartate or quadruple the dose for L-thiocitrulline of $N^\omega$-methyl-L-citrulline or $N^\omega$-ethyl-L-citrulline or L-norvaline or L-isoleucine.

EXAMPLE XV

A patient with Gram negative septicemia and blood pressure of 80/55 mm Hg is administered dopamine at 10 µg/kg/min to acutely increase blood pressure and concurrently is intravenously administered an initial bolus dose of L-thiocitrulline of 20 mg/kg and thereafter L-thiocitrulline as a sustained infusion at a dose of 10 mg/kg/hr. Blood pressure becomes normal within minutes and this state is sustained. The patient is released within 2 days.

When the double the dose for L-thiocitrulline of D-aspartate or quadruple the dose for L-thiocitrulline of $N^\omega$-methyl-L-citrulline or L-norvaline or L-isoleucine are substituted for the L-thiocitrulline, blood pressure increases acutely to the mild hypotensive range and the patient becomes normotensive by 24 to 72 hours.

EXAMPLE XVI

A patient with a Gram negative septicemia and blood pressure of 80/55 mm Hg is administered $N^G$-methyl-L-arginine in a bolus dose of 20 mg/kg intravenously in saline and thereafter is given a sustained infusion of $N^G$-methyl-L-arginine at a dose of 10 mg/kg/hr. $N^\omega$-Methyl-L-citrulline (40 mg/kg) is given intravenously in 50 ml saline over 3–6 hours starting at the time of the bolus dose of $N^G$-methyl-L-arginine. Blood pressure becomes mildly hypotensive or normal within minutes of administration of the bolus dose of $N^G$-methyl-L-arginine and this state is sustained.

Similar results are obtained as are obtained with $N^\omega$-methyl-L-citrulline when $N^\omega$-ethyl-L-citrulline at 40 mg/kg or D-aspartate at 20 mg/kg or L-norvaline at 20 mg/kg or L-isoleucine at 40 mg/kg is given in place of the $N^\omega$-methyl-L-citrulline.

EXAMPLE XVII

A patient with rheumatoid arthritis with swelling localized to two painful joints is administered L-thiocitrulline at a dose of 0.1 mg/kg intra-articularly into each joint. Local synovitis is reduced within 12 to 72 hours.

When $N^\omega$-methyl-L-citrulline or L-norvaline or L-isoleucine is given intra-articularly into each joint at a dose of 0.2 mg/kg or D-aspartate is given at a dose of 0.1 mg/kg intra-articularly into each joint, local synovitis is reduced within 12 to 72 hours.

EXAMPLE XVIII

Sprague-Dawley rats are injected with 25 cc air subdermally in the dorsal area in accordance with the air pouch inflammatory model (Selye, H., Proc. Soc.. Exper. Biol. and Med., 82,328–333 (1953). Into the air pouch formed, an inflammatory simulus, croton oil (0.5% in 0.5 ml corn oil), is injected. The rats in one group do not receive drug. The rats in the second group receive L-thiocitrulline at 20 mg/kg intraperitoneally with repeat doses at 6–24 hour intervals. At the end of 5 days, the group of rats given L-thiocitrulline have significantly less nitrite in the fluid exudate contained in the granulomycous lesion and less inflammation than the rats in the other group.

Similar results as to what are obtained with L-thiocitrulline are obtained when 20 mg/kg of D-aspartate or 40 mg/kg of $N^\omega$-methyl-L-citrulline or $N^\omega$-propyl-L-citrulline or L-norvaline or L-isoleucine is substituted for the L-thiocitrulline.

EXAMPLE XIX 16.86 gm (0.1 mol) of L-ornithine hydrochloride is dissolved in 200 ml of 1 M NaOH. To the clear solution is added 5.71 gm of methyl isocyanate (0.1 mol) dropwise at room temperature. The pH is maintained at 9.5–10.5 by occasional cautious additon of 1M NaOH. After stirring overnight at room temperature, the reaction mixture is reduced to dryness by rotary evaporation at reduced pressure. The residue is suspended in concentrated HCl, and the precipitate of NaCl is filtered off. The filtrate, which contains $N^\omega$-methyl-L-citrulline is evaporated to dryness under reduced pressure and redissolved in a small volume of water. That solution is applied to a column 2.0 by 50 cm of Dowex 50 ($Na^+$ form). The column is washed with 2 L of distilled water and fractions of approximately 25 ml are collected sequentially. Under these conditions of chromatography, $N^\omega$-methyl-L-citrulline is eluted and residual unreacted L-ornithine remains bound to the Dowex resin. Fractions containing $N^\omega$-methyl-L-citrulline (detected using a conventional ninhydrin spot assay) are pooled, rotary evaporated to dryness under reduced pressure, and the residual oil is crystallized from ethanol/water. The overall yield is approximately 75% based on the amount of ornithine used.

$N^\omega$-Alkyl-L-citrullines with different $N^\omega$-alkyl groups from methyl are prepared by substituting an equivalent molar amount of the corresponding alkyl isocyanate for the methyl isocyanate.

Many variations will be obvious to those skilled in the art. Thus, the invention is defined by the claims.

What is claimed is:

1. A method of prophylaxis or treatment of a subject for systemic hypotension caused by pathological overproduction of nitric oxide from arginine in vascular cells in said subject induced by therapy with a cytokine or by exposure to a bacterial endotoxin, said method comprising administering to a subject expected to develop or having such systemic hypotension a therapeutically effective amount of an argininosuccinate synthetase activity reducing agent.

2. The method of claim 1 wherein the argininosuccinate synthetase activity reducing agent is an argininosuccinate synthetase induction blocking agent.

3. The method of claim 2 wherein the argininosuccinate synthetase induction blocking agent is also a nitric oxide synthase induction blocking agent and is an antibiotic that binds to DNA sequences present in the upstream regulatory region of the argininosuccinate synthetase gene.

4. The method of claim 3 wherein the antibiotic is selected from the group consisting of mithramycin, chromomycins and olivomycins.

5. The method of claim 4 wherein the antibiotic is mithramycin.

6. The method of claim 1 wherein the argininosuccinate synthetase activity reducing agent is an argininosuccinate synthetase inhibitor.

7. The method of claim 6 wherein the argininosuccinate synthetase inhibitor is an L-citrulline antagonist.

8. The method of claim 7 wherein the L-citrulline antagonist is not L-thiocitrulline or L-homothiocitrulline.

9. The method of claim 8 wherein the L-citrulline antagonist is $N^\omega$-alkyl-L-citrulline wherein the alkyl contains 1 to 6 carbon atoms.

10. The method of claim 9 wherein the L-citrulline antagonist is $N^\omega$-methyl-L-citrulline.

11. The method of claim 6 wherein the argininosuccinate synthetase inhibitor is an L-aspartate antagonist.

12. The method of claim 11 wherein the L-aspartate antagonist is D-aspartate.

13. A method for treatment of a subject for systemic hypotension caused by pathological overproduction of nitric oxide from arginine in vascular cells in said subject induced by therapy with a cytokine or by exposure to a bacterial endotoxin, said method comprising administering to a subject having such systemic hypotension a therapeutically effective amount of an $\alpha_1$-adrenergic agonist and an amount of argininosuccinate synthetase activity reducing agent to restore vascular contractile sensitivity to the effects of the $\alpha_1$-adrenergic agonist.

14. The method of claim 13 wherein the argininosuccinate synthetase activity reducing agent is an argininosuccinate synthetase induction blocking agent.

15. The method of claim 14 wherein the argininosuccinate synthetase induction blocking agent is also a nitric oxide synthase induction blocking agent and is an antibiotic that binds to DNA sequences present in the upstream regulatory region of the argininosuccinate synthetase gene.

16. The method of claim 15 wherein the antibiotic is selected from the group consisting of mithramycin, chromomycins and olivomycins.

17. The method of claim 16 wherein the antibiotic is mithramycin.

18. The method of claim 13 wherein the argininosuccinate synthetase activity reducing agent is an argininosuccinate synthetase inhibitor.

19. The method of claim 18 wherein the argininosuccinate synthetase inhibitor is an L-citrulline antagonist.

20. The method of claim 19 wherein the L-citrulline antagonist is not L-thiocitrulline or L-homothiocitrulline.

21. The method of claim 20 wherein the L-citrulline antagonist is $N^\omega$-alkyl-L-citrulline wherein the alkyl contains 1 to 6 carbon atoms.

22. The method of claim 21 wherein the L-citrulline antagonist is $N^\omega$-methyl-L-citrulline.

23. The method of claim 18 wherein the argininosuccinate synthetase inhibitor is an L-aspartate antagonist.

24. The method of claim 23 wherein the L-aspartate antagonist is D-aspartate.

25. A method for treating a subject for systemic hypotension caused by pathological overproduction of nitric oxide from arginine in vascular cells in said subject induced by therapy with a cytokine or by exposure to a bacterial endotoxin, said method comprising administering to said subject a therapeutically effective amount of an arginine antagonist of nitric oxide synthesis by nitric oxide synthase and a therapeutically effective amount of an argininosuccinate synthetase activity reducing agent selected from the group consisting of orgininosuccinate synthetase induction blocking agents and argininosuccinate synthetase inhibitors which do not block the activity of inducible nitric oxide synthase.

26. The method of claim 25 wherein the argininosuccinate synthetase activity reducing agent is an arginiosuccinate synthetase induction blocking agent.

27. The method of claim 26 wherein the argininosuccinate synthetase induction blocking agent is also a nitric oxide synthase induction blocking agent and is an antibiotic that binds to DNA sequences present in the upstream regulatory region of the argininosuccinate synthetase gene.

28. The method of claim 27 wherein the antibiotic is selected from the group consisting of mithramycin, chromomycins and olivomycins.

29. The method of claim 28 wherein the antibiotic is mithramycin.

30. The method of claim 25 wherein the argininosuccinate synthetase activity reducing agent is an argininosuccinate synthetase inhibitor which does not block the activity of inducible nitric oxide synthase.

31. The method of claim 30 wherein the argininosuccinate synthetase activity reducing agent is an L-citrulline antagonist.

32. The method of claim 31 wherein the L-citrulline anagonist is $N^{\omega}$-alkyl-L-citrulline wherein the alkyl contains 1 to 6 carbon atoms.

33. The method of claim 32 wherein the L-citrulline antagonist is $N^{\omega}$-methyl-L-citrulline.

34. The method of claim 30 wherein the argininosuccinate synthetase activity reducing agent is an L-aspartate antagonist.

35. The method of claim 34 wherein the L-aspartate antagonist is D-aspartate.

* * * * *

UNITED STATES PATENT AND TRADEMARK OFFICE
CERTIFICATE OF CORRECTION

PATENT NO. : 5,545,625
DATED : August 13, 1996
INVENTOR(S) : STEVEN S. GROSS, et al.

It is certified that error appears in the above-indentified patent and that said Letters Patent is hereby corrected as shown below:

Claim 25 (column 19, line 3), change "orgininosuccinate" to --argininosuccinate--.

Claim 26 (column 19, line 8), change "arginiosuccinate" to --argininosuccinate--.

Signed and Sealed this

Eleventh Day of March, 1997

Attest:

BRUCE LEHMAN

*Attesting Officer*   Commissioner of Patents and Trademarks